(12) United States Patent
Letizia et al.

(10) Patent No.: US 11,596,540 B2
(45) Date of Patent: Mar. 7, 2023

(54) DEVICES AND METHOD FOR BRUXISM MANAGEMENT

(71) Applicant: AESYRA SA, Lausanne (CH)

(72) Inventors: Marco Letizia, Ecublens (CH); Pietro Maoddi, Préverenges (CH)

(73) Assignee: AESYRA SA, Lausanne (CH)

( * ) Notice: Subject to any disclaimer, the term of this patent is extended or adjusted under 35 U.S.C. 154(b) by 193 days.

(21) Appl. No.: 16/955,447

(22) PCT Filed: Dec. 22, 2017

(86) PCT No.: PCT/IB2017/058358
§ 371 (c)(1),
(2) Date: Jun. 18, 2020

(87) PCT Pub. No.: WO2019/123232
PCT Pub. Date: Jun. 27, 2019

(65) Prior Publication Data
US 2020/0345536 A1    Nov. 5, 2020

(30) Foreign Application Priority Data

Dec. 22, 2017    (WO) .................. PCT/IB2017/058358

(51) Int. Cl.
*A61F 5/56* (2006.01)
*A61B 5/0205* (2006.01)
(Continued)

(52) U.S. Cl.
CPC .............. *A61F 5/566* (2013.01); *A61B 5/024* (2013.01); *A61B 5/02055* (2013.01);
(Continued)

(58) Field of Classification Search
CPC .............. A61F 5/566; A61F 2005/563; A61B 5/02055; A61B 5/024; A61B 5/228;
(Continued)

(56) References Cited

U.S. PATENT DOCUMENTS 6,089,864 A *   7/2000   Buckner ................... A61F 5/56
                                                    433/68
2012/0123225 A1*   5/2012   Al-Tawil ................. A61F 5/566
                                                    600/301
(Continued)

FOREIGN PATENT DOCUMENTS

EP      0379524 B1 *   2/1994   ............. G01L 1/205
EP      0379524 B1     2/1994
(Continued)

OTHER PUBLICATIONS

International Search Report; European Patent Office; International Application No. PCT/IB2018/060229; dated May 21, 2019; 6 pages.
Written Opinion of the International Searching Authority; European Patent Office; International Application No. PCT/IB2018/060229; dated May 21, 2019; 8 pages.

*Primary Examiner* — Jacqueline Cheng
*Assistant Examiner* — Tho Q Tran
(74) *Attorney, Agent, or Firm* — Taft Stettinius & Hollister LLP

(57) ABSTRACT

A dental appliance including a dielectric substrate with one or more electric areas having one or more integrated circuits, one or more electric lines, and optionally one or more shielding lines. The dental appliance further includes one or more ground areas including one or more ground pads, one or more sensing areas including one or more sensing pads, and optionally one or more shielding pads. The dental appliance is configured to monitor dental contact, dental forces, and/or for detecting teeth clenching and/or grinding.

18 Claims, 11 Drawing Sheets

(51) Int. Cl.
  *A61B 5/22*    (2006.01)
  *A61B 5/318*   (2021.01)
  *A61B 5/369*   (2021.01)
  *A61B 5/00*    (2006.01)
  *A61B 5/024*   (2006.01)

(52) U.S. Cl.
  CPC .............. *A61B 5/228* (2013.01); *A61B 5/318* (2021.01); *A61B 5/369* (2021.01); *A61B 5/4557* (2013.01); *A61B 5/682* (2013.01); *A61F 2005/563* (2013.01)

(58) Field of Classification Search
  CPC ....... A61B 5/318; A61B 5/369; A61B 5/4557; A61B 5/682
  See application file for complete search history.

(56) References Cited

U.S. PATENT DOCUMENTS

| | | |
|---|---|---|
| 2015/0305671 A1 | 10/2015 | Toon et al. |
| 2016/0242692 A1 | 8/2016 | McAuliffe et al. |
| 2016/0242951 A1 | 8/2016 | Berk et al. |
| 2018/0310881 A1* | 11/2018 | Yoon ................. A61B 5/02416 |

FOREIGN PATENT DOCUMENTS

| | | |
|---|---|---|
| EP | 1110501 A1 | 6/2001 |
| EP | 1148816 B1 | 10/2007 |

\* cited by examiner

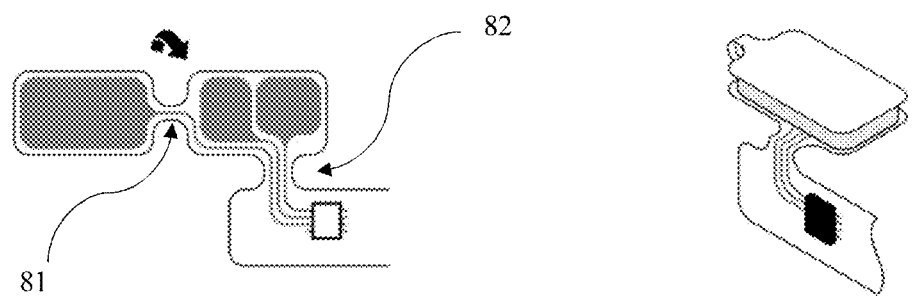
Figure 5A
Figure 5B
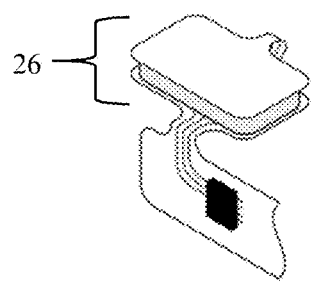
Figure 5C
Figure 5D

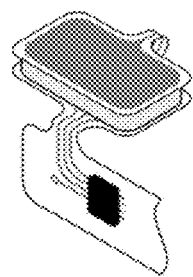
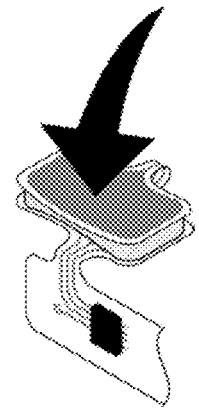
Figure 8A     Figure 8B
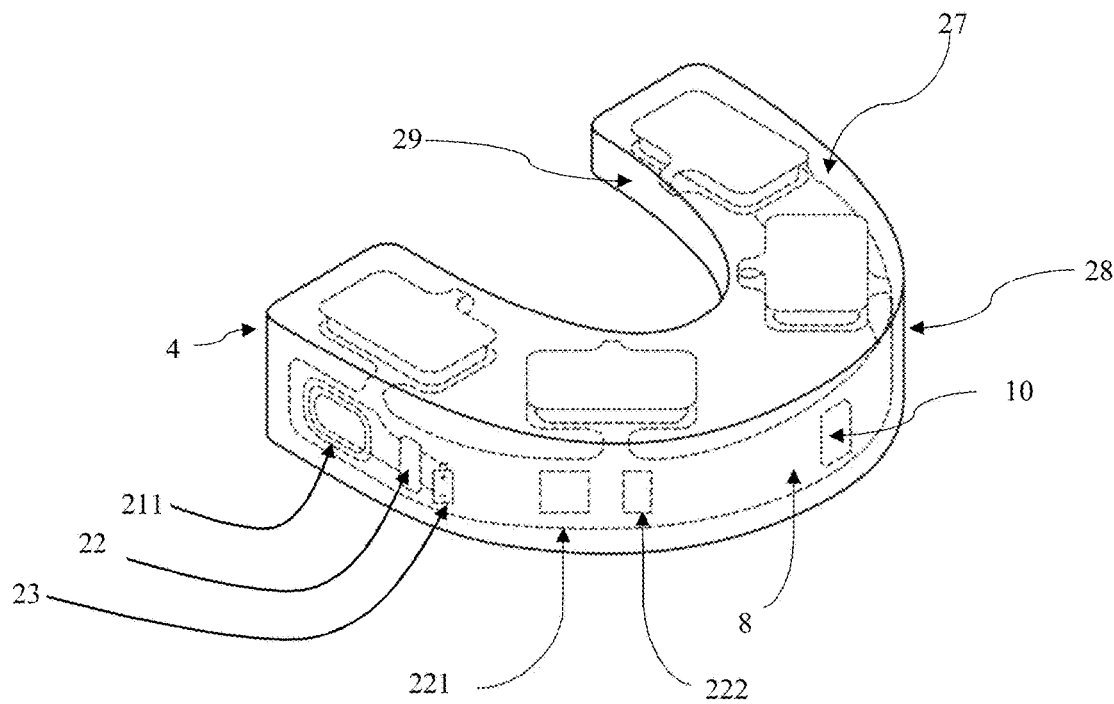
Figure 9

DEVICES AND METHOD FOR BRUXISM MANAGEMENT

CROSS REFERENCE TO RELATED APPLICATIONS

This application is a U.S. national stage filing of International Patent Application No. PCT/IB2018/060229 filed Dec. 18, 2018, which claims priority to International Patent Application No. PCT/IB2017/058358 filed Dec. 22, 2017, the contents of each application hereby incorporated by reference in their entirety.

TECHNICAL FIELD

The present invention relates to a dental device, a dental appliance or a dental splint or a mouth-guard, a splint assembly or a splint system, a use of thereof for monitoring, preventing and/or treating bruxism and a method for preventing and/or treating bruxism.

BACKGROUND ART

Bruxism is a disorder relative to a reflexive chewing activity such as teeth clenching or grinding, which has not been completely clarified yet. While sleeping, people suffering from bruxism exhibit about 10-40 grinding episodes per night lasting about 10-20 seconds each, during which a jaw force that can exceed 100 kg is exerted. This disorder does adversely affect health. The reported health complications are teeth wear, teeth shortening, dental prostheses complications, temporomandibular joint complications (clicking and popping of the jaw), masseter hypertrophy, morning headache, and facial pain. The aesthetics of the smile are affected as well.

So far, there is no therapy that can definitively cure bruxism. Current treatments for bruxism can be divided into three major categories: oral devices such as dental appliances, drugs, including, for example, Clonidine, Clonazepam and L-dopa, and biofeedback devices. However such treatments present many drawbacks. Oral devices such as dental appliances offer passive teeth protection and can increase bruxism activity during the first weeks of use. Moreover, since the causes of the disorder are not treated, said bruxism activity continues. Although the use of drugs reduces bruxism in the beginning of the treatment, they may cause addictions and drowsiness and are not suitable for long-term treatment because of their negative effect on professional life (e.g. impossibility of operating vehicles). Further, the use of drugs does not remove the health and physical complications. Although biofeedback devices are moderately effective in reducing bruxism by detecting bruxism activity through sensors (electromyography, sounds) and alerting the patient through a sound or vibration, such systems do not prevent teeth grinding completely and bruxism episodes are still present. Furthermore, when using such systems, dental implants and dental prostheses are still affected by remarkable mechanical overload (compressive loading).

Existing intraoral sensors for the bruxism detection are based on assemblies (typically piezo-resistive sensors) connected mechanically or by soldering to an electronic board for signal processing embedded in the splint. Sensors comprise many superimposed layers resulting in bulky systems to be placed in the mouth and exhibit a typical on/off response of a switch detecting bruxism qualitatively. Furthermore, such electro-mechanical assemblies have low mechanical tolerances, high electrical noise levels, and low measurement reproducibility. These drawbacks strongly limit the clinical application of such dental devices, since they cannot provide quantitative data on the bruxism activity and their fabrication involves several different manufacturing processes, which increase their overall cost.

US 2015/0305671A1 and US 2016/0242951A1 disclose sensor assemblies based on capacitive or resistive proximity measurements. The variation of the electric field measured by the patch is due to the electric properties and to the proximity of the external body. The proximity of the external body is related to the mechanical load by virtue of the compression of the material separating the external body from the patch. Indeed a real tooth and a dental prosthesis are made of different materials, which electrically behave differently in presence of an electric field, and will provide a different output on the sensors for the same applied load. For this reason, such sensors can only provide a qualitative assessment of the dental load and bruxism cannot be assessed quantitatively.

Existing sensors for bruxism detection integrated into oral appliances, dental splints or mouth-guards are powered by wirelessly rechargeable batteries. Wireless inductive charging is preferred for smart appliances to avoid connector interfaces and improve insulation. The battery charging process requires the device and the charger to be close to each other or in direct contact. In the case of dental splints, users typically store the splint in a plastic storage case, wherein the splint may be charged. Wireless charging only occurs if the charger and the splint are properly aligned in an optimal position for charging, which may not be easily found by the user. This will impair the performance of the charging process (uncharged battery or incompletely charged battery) and the devices warm up due to excessive electric current involved in the process. The warm-up of the dental appliance, often made by thermoformable plastics (e.g., Ethylene Vinyl Acetate) with melting points around 80° C. and comprising electronics, will deform the appliance material and shape. The change in the splint shape makes traditional chargers difficult to be used effectively.

There is a need for sensor assemblies being able to measure quantitatively and reliably—and not only qualitatively—the value of the load and the dynamic behavior of the force applied to the sensor.

There is a need to have a treatment of the bruxism, which may be a long-term treatment with no side effect but also which prevents the episodes of bruxism.

There is also a need to have a charger device for electronic dental appliances or splints, which provides an efficient and easy wireless charging of the batteries without warming up the assemblies and deforming the same.

The present invention addresses the problems depicted above.

SUMMARY OF THE INVENTION

The invention provides a solution to all the aforementioned drawbacks.

Surprisingly, the inventors have found that the integration of a sensing region in a dielectric substrate, said substrate being in one piece, which is used to support integrated circuit (IC) units, the whole included in a dental appliance enables intraoral sensors to reliably detect user biting parameters. The presence of the human body or materials like prosthesis in the proximity of the sensor may influence the measurements. However, since the sensory part of the dielectric substrate is electrically shielded with ground pads and/or with active shielding pads, said impact or influence is rather marginal. The sensing region, in particular the sensor, behaves elastically with respect to the human bite force since the dielectric substrate, the part of the dielectric substrate housing the sensing region and the sensor are made by elastic materials. The dielectric substrate housing different electrical features (electric line, pads, and sensors) is integrated in a dental appliance to detect bruxism and dental forces patterns allowing the evaluation of the severity of the condition. The quality of measurements performed by the dental appliance of the invention (mechanical tolerances, electrical noise level and reproducibility), and the resulting clinical outcome (quantitative detection of dental forces and jaw movement patterns) with respect to existing solutions are remarkably improved.

The electrically shielding of the sensing pad of a force sensor in a dental appliance further improves measuring and recording dental forces signals quantitatively, drastically reducing artefacts from interferences. The presence of shielding pads on the sensor allows a reliable characterization of the value of the load and the dynamic behavior of the force applied to the sensor. Without shielding pad, the sensors readings can be affected not only by the applied mechanical load but also by the nature of the materials in their proximity. Such proximity influences the electric charge distribution and, thus, the electrical field around the conductive patch. Thus for the same applied dental load on one sensor, different output can be recorded providing unreliable measures unsuitable for monitoring and assess bruxism. The presence of shielding pads protects the sensors of these biased measures.

Furthermore since the dielectric substrate housing sensors, sensing pads, ground pads, and at least an integrated circuit is made of one single piece, the costs for fabricating a dental appliance with such dielectric substrate can be maintained low by decreasing the number of fabrication steps. It also allows providing a dental appliance which may incorporate further means for recording additional signals in the field of the study, monitoring and/or treatment of teeth clenching and grinding and/or bruxism, without involving different types of manufacturing processes and without providing bulky systems to be bitten.

According to one aspect, the invention relates to a dental appliance comprising a dielectric substrate comprising
- one or more electric areas comprising one or more integrated circuits and one or more electric lines,
- one or more ground areas comprising one or more ground pads,
- one or more sensing areas comprising one or more sensing pads, characterized in that
- the one or more electric areas, the one or more ground areas, and the one or more sensing areas are housed on the same dielectric substrate being in one piece comprising a dielectric material;
- one or more sections of the dielectric substrate are bent;
- one sensing area faces one ground area; and
- said one sensing area facing one ground area is separated by a layer comprising an elastic material, and forms a sensor.

According to another aspect, the present invention also relates to a device assembly for reducing teeth clenching and/or grinding and/or preventing bruxism comprising
- a sensing unit for detecting teeth clenching and/or grinding,
- a biofeedback unit, and
- at least one auxiliary unit,
- a signal processing means, characterized in that
said sensing unit, said biofeedback unit, said at least one auxiliary unit and said signal processing means are included in a same device or in two or more devices;
the at least one auxiliary unit is a sensor for measuring one or more sensor signals selected from respiratory airflow, snoring, blood oxygen saturation, pH, blood pressure, heart rate, electrocardiographic activity, electroencephalographic activity, body temperature, body position, body movement, and eye movement;
the signal processing means comprises a receiver means to detect one or more sensor signals, and/or one or more dental forces signals, a monitoring means to detect the variation of the intensity and/or the frequency of said signals vs. time, and a transmitter means to generate an action signal in response to said one or more variations of one or more sensor signals and/or said dental forces signals; and
the biofeedback unit is a responsive means in communication with the signal processing means and responding to the action signal and is selected from means providing vibrating signal, tactile signal, acoustic signal, electrical stimulation signal and/or optical signal.

According to a further aspect, the present invention also a dental appliance storage case comprising
a base;
a cover hinged to the base;
two appendices orientated normal to the base;
characterized in that
the base comprises a power supply, a module to exchange data and/or a means for producing alternating current;
at least one appendix comprises a coil electrically connected to the power supply, the two appendices being separated by a distance inferior to the distance separating one outer edge to the other outer edge of the ends of a dental appliance, said dental appliance comprising a coil connected to a battery and being flexible.

In another aspect, the invention also relates to a method for reducing teeth clenching and/or grinding and/or preventing bruxism comprising the steps of
obtaining at least one sensor signal selected from respiratory airflow, snoring, blood oxygen saturation, pH, blood pressure, heart rate, electrocardiographic activity, electroencephalographic activity, body temperature, body position, body movement, and eye movement measured by an auxiliary unit;
processing at least one sensor signal and determining at least a variation of the intensity and/or the frequency of said signals vs. time;
providing a stimulus selected from vibrating signal, tactile signal, acoustic signal, electrical stimulation signal and/or optical signal in response to the variation of the intensity and/or the frequency of said at least one sensor signal vs. time.

Further aspects and preferred embodiments of the invention are detailed herein below and in the appended claims. Further features and advantages of the invention will become apparent to the skilled person from the description of the preferred embodiments given below.

BRIEF DESCRIPTION OF THE DRAWINGS

Other features and advantages of the present invention will appear more clearly from the detailed description of one embodiment of the invention which is present solely by way of a non-restricted example and illustrated by the attached drawings in which:

FIG. 5A and FIG. 5B respectively illustrate a view or a perspective view of a detail of the dielectric substrate as shown in, respectively, FIG. 4A and FIG. 4B. FIG. 5C and FIG. 5D illustrate the same as in FIGS. 5A and 5B, excepted that the detail of the dielectric substrate is according to a further embodiment.

FIG. 8A illustrates a perspective view of a dielectric substrate with a sensor having uncompressed material. FIG. 8B illustrates a perspective view of a dielectric substrate with a sensor under pressure.

FIG. 9 illustrates a dental appliance according to one embodiment including the dental substrate (in dashed line).

DETAILED DESCRIPTION OF THE INVENTION

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

Figure 7A:
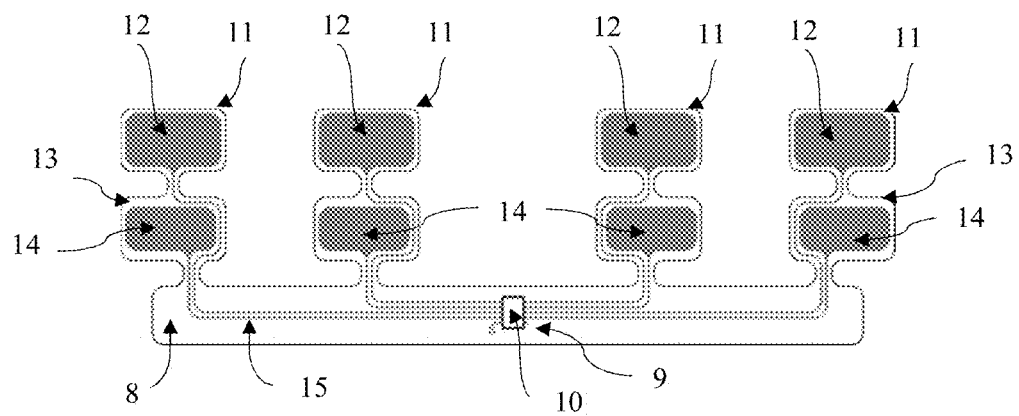
FIG. 7A shows a view of the front side of the dielectric substrate.
Figure 7B:
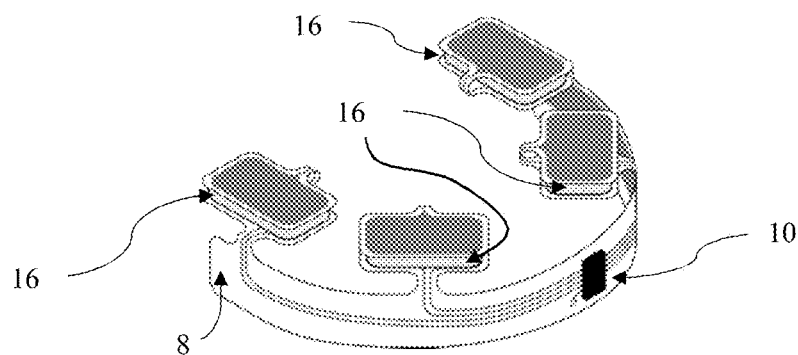
FIG. 7B shows a perspective view of the dielectric substrate according to one embodiment.
Figure 12A:
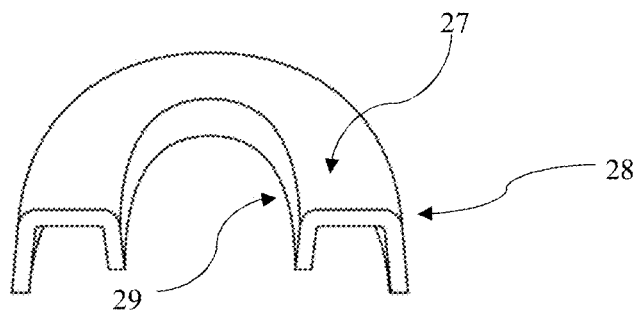
FIG. 12A illustrates a view from the back side of the dental appliance, the dielectric substrate included in the dental appliance being not shown.

FIG. 9 and FIG. 12A illustrate a dental appliance comprising a dielectric substrate as illustrated in FIG. 7B and FIG. 7A. Although the illustrated dental appliances have a shape fitting the maxillary dental arch and/or the mandibular dental arch, the shape of the dental appliance is not limited to the shape of the illustrated dental appliances.

The invention provides a dental appliance 4 comprising a dielectric substrate 8, which comprises one or more electric areas 9 comprising one or more integrated circuits 10 and one or more electric lines 15, one or more ground areas 11 comprising one or more ground pads 12, one or more sensing areas 13 comprising one or more sensing pads 14; characterized in that the one or more electric areas, the one or more ground areas, and the one or more sensing areas are housed on the same dielectric substrate being in one piece and comprising a dielectric material; in that one or more sections of the dielectric substrate are bent; in that one sensing area faces one ground area; and said one sensing area facing one ground area is separated by a layer comprising an elastic material 16, and forms a sensor 26.

According to one embodiment, the dielectric substrate 8 further comprises one or more shielding lines 18; and one or more shielding pads 17. Then said one or more electric areas, the one or more ground areas, the one or more sensing areas and one or more shielding pads are housed on the same dielectric substrate being one piece comprising a dielectric material. One or more sections of the dielectric substrate are bent. One sensing area faces one ground area and said one sensing area facing one ground area is separated by a layer comprising an elastic material 16, and forms a sensor 26.

Said one or more electric areas 9, said one or more ground areas 11, said one or more sensing areas 13 and said one or more shielding pads 17 are housed on the same dielectric substrate 8. Said dielectric substrate 8 is in one piece comprising a dielectric material, i.e. said dielectric substrate is free of soldering and/or assembly of several pieces of dielectric substrate and is made in one piece. The one or more electric areas, ground areas and sensing areas are housed on the same side of the dielectric substrate 8, said side being front side 8a. The one or more shielding pads, if present, are housed on the side of the dielectric substrate opposed to the front side being the back side 8b of the dielectric substrate, behind the sensing area and/or the ground area. The dielectric substrate 8 housing the ground area 11 extends from the dielectric substrate housing the sensing area 13, both areas being bound by a section 81 of the dielectric substrate. As illustrated in FIGS. 4A-B, 5A-D, 6A-C, the dielectric substrate 8 is bent at the level of the section 81, the ground area 11 being placed on a layer comprising an elastic material 16 separating the sensing area 13 from said ground area 11. The ground area 11 bent on the sensing area 13, the sensing area and the layer comprising the elastic material 16 forms a sensor 26.

The dielectric substrate 8 housing the sensing area 13 extends from the dielectric substrate housing the electric area 9, both areas being bound by a section 82 of the dielectric substrate. As illustrated in FIGS. 4A-B, 5A-D, 7B-C and 9, the section 82 of the dielectric substrate is bent in order that the dielectric substrate fits the shape of the dental appliance 4 and that the sensor 26 is on the sensor side 27 of said dental appliance.

The dental appliance may comprise one sensor, of which shape covers at least one or two teeth. Preferably the dental appliance may comprise at least two sensors. It may comprise more than two sensors, the number of the sensors being determined by the size of one sensor and the size or length of the dental arch.

According to one embodiment, the one or more ground pads 12 and the one or more sensing pads 14 are electrically connected to one or more integrated circuits 10 through the electric lines. The one or more shielding pads, if present, are electrically connected to one or more integrated circuits 10 through the shielding lines 18.

Figure 1A:
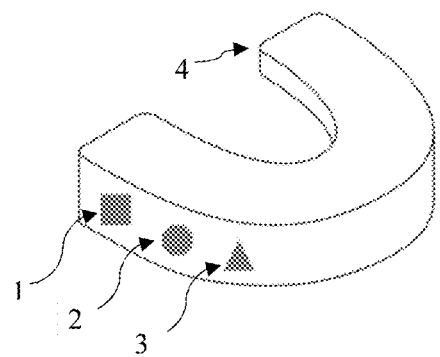
FIG. 1A, FIG. 1B, FIG. 1C, and FIG. 1D illustrates device assemblies, wherein the sensing unit 1, biofeedback unit 2 and an auxiliary unit are place on a same device or on several devices, one device being a dental appliance.
Figure 1B:
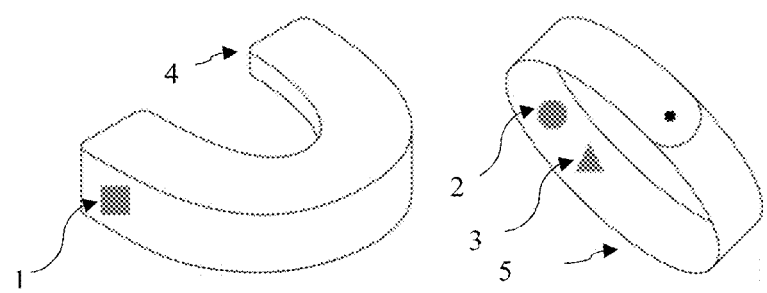
Figure 1C:
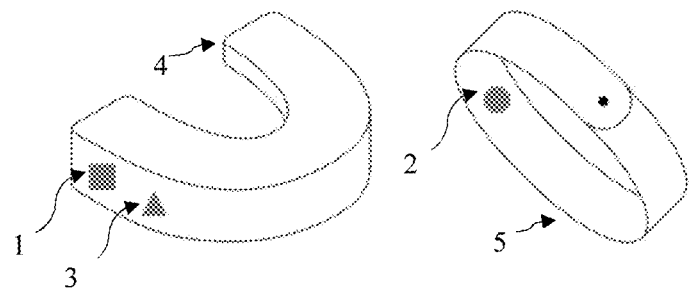
Figure 1D:
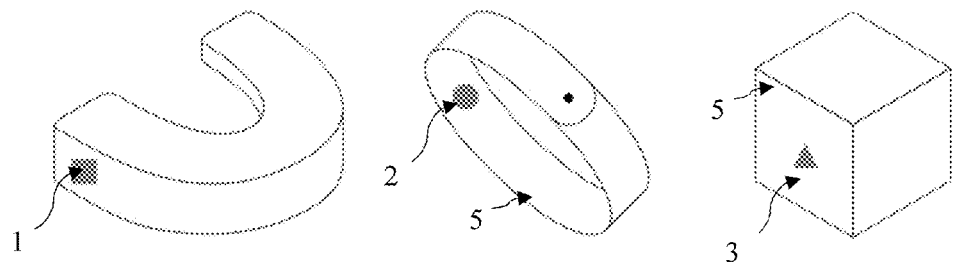
Figure 2A:
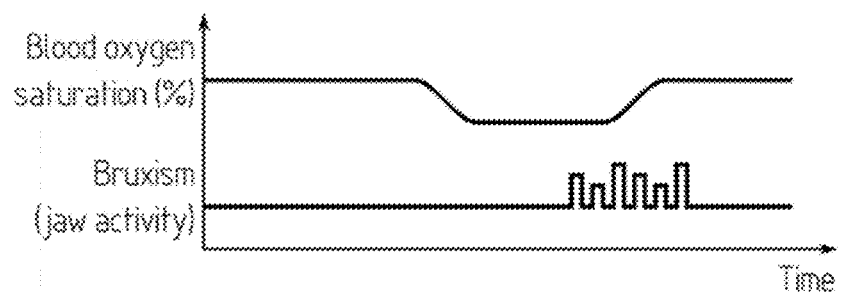
FIG. 2A shows a graphic of measurements of the percentage of blood oxygen saturation and the jaw activity (masticatory muscle activity) during sleep and their variation of said measurements during an episode of bruxism of a patient without treatment of bruxism or without using a biofeedback unit.
Figure 2B:
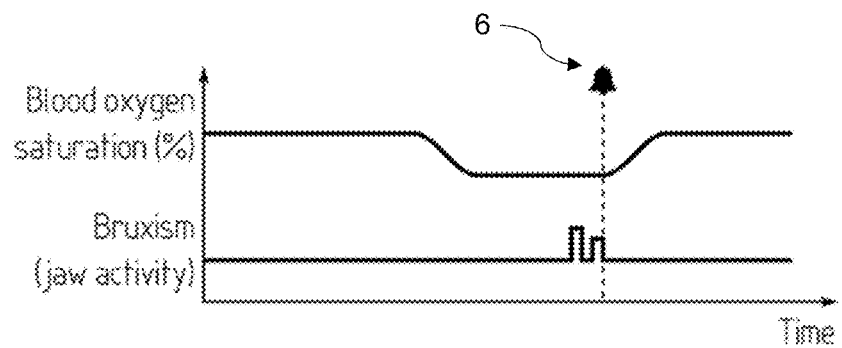
FIG. 2B shows a graphic of measurement of the same parameters as in FIG. 2A in a patient treated with a device assembly having a usual biofeedback unit reacting only to the masticatory activity.
Figure 2C:
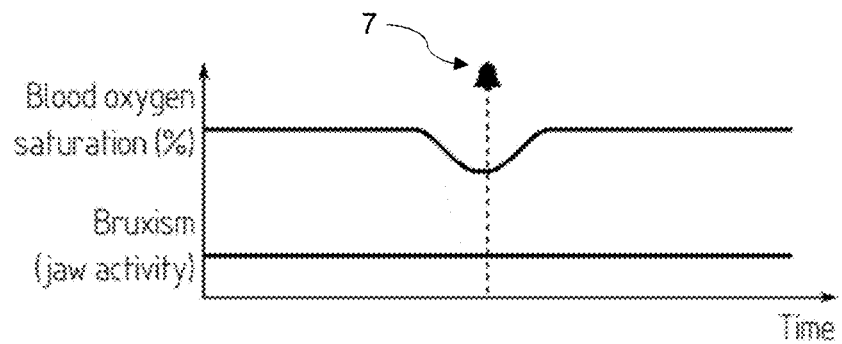
FIG. 2C illustrates the same as in FIG. 2B but the patient being treated with a device assembly of the invention having a biofeedback unit reacting to the variation of one or more parameters such as the percentage of blood oxygen saturation or in addition of the masticatory activity to prevent bruxism episodes.
Figure 3A:
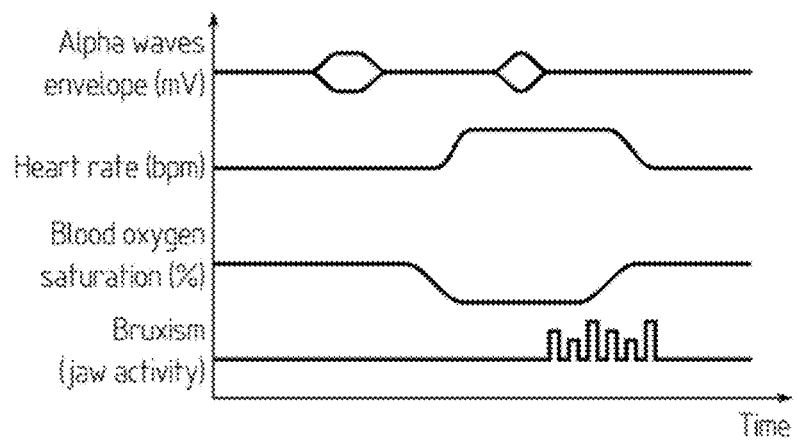
FIG. 3A, FIG. 3B and FIG. 3C show the same as in, respectively, FIG. 2A, FIG. 2B and FIG. 2C but body parameters: alpha waves and heart rate are measured in addition to the percentage of blood oxygen saturation and their variation is used to trigger the biofeedback unit.
Figure 3B:
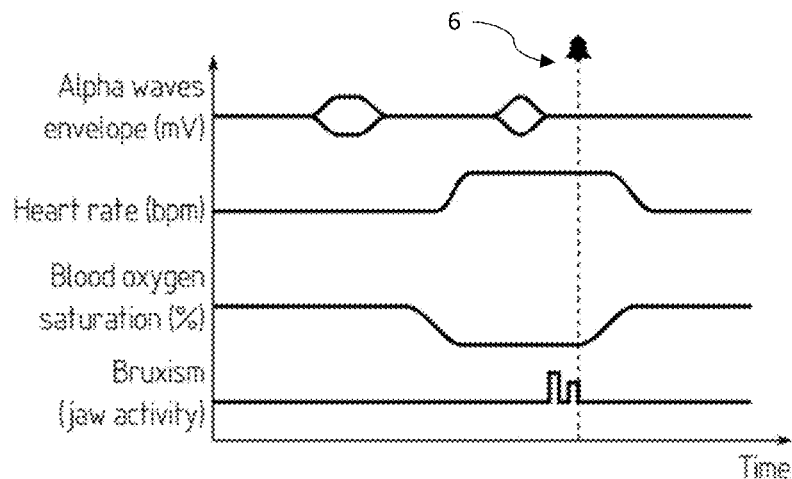
Figure 3C:
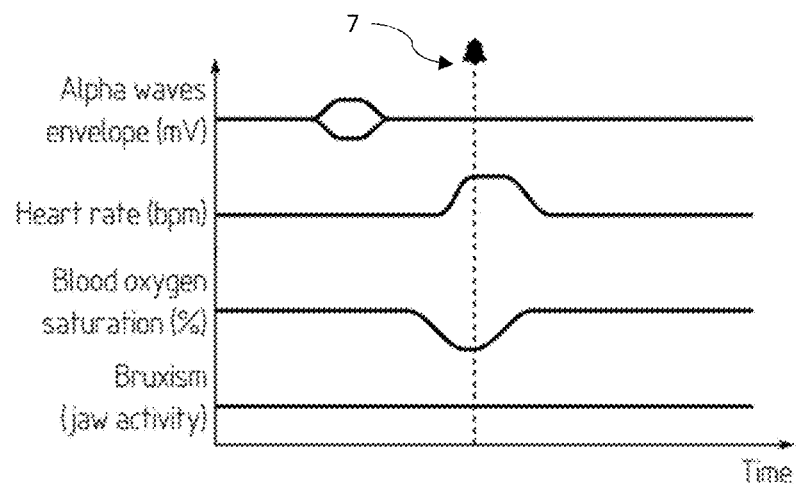
Figure 4A:
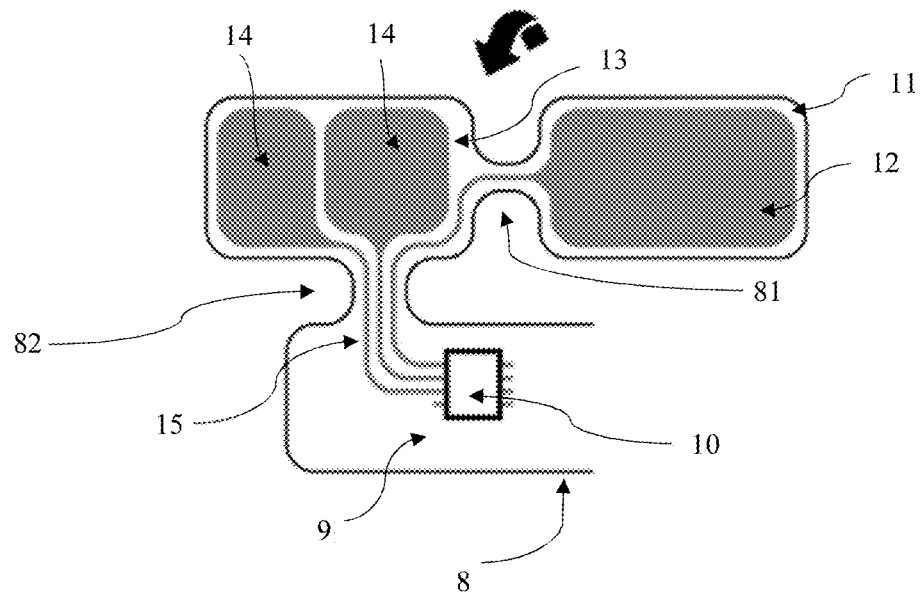
FIG. 4A illustrates a view of a detail of the dielectric substrate housing a sensing area, a ground area and an electrical area.
Figure 4B:
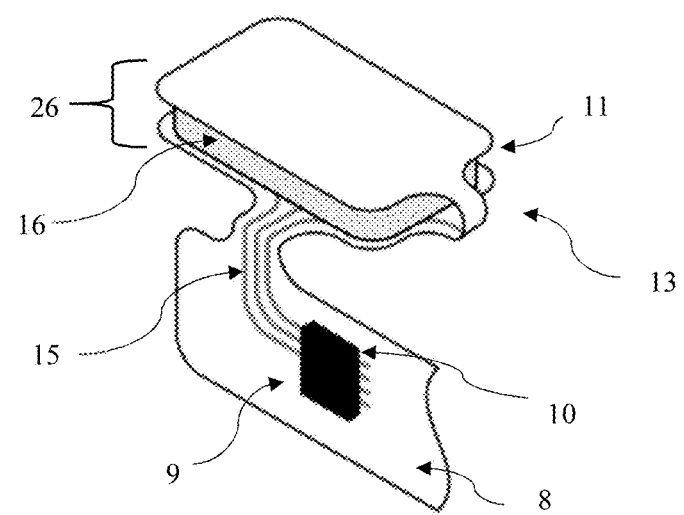
FIG. 4B illustrates a perspective view of a detail of the dielectric substrate in FIG. 4A, wherein the sensing area bent on the ground area and separated from said ground area by a layer of elastic material forms a sensor.
Figure 6A:
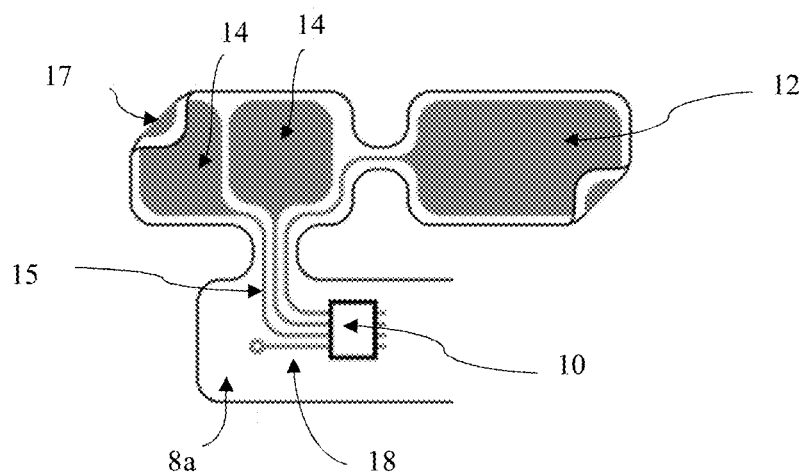
FIG. 6A illustrates a view of a detail of the front side of the dielectric.
Figure 6B:
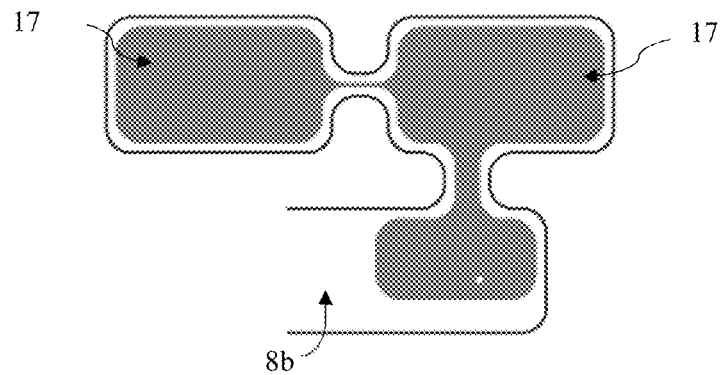
FIG. 6B illustrates a view of a detail of the back side of the dielectric substrate housing shielding pad.
Figure 6C:
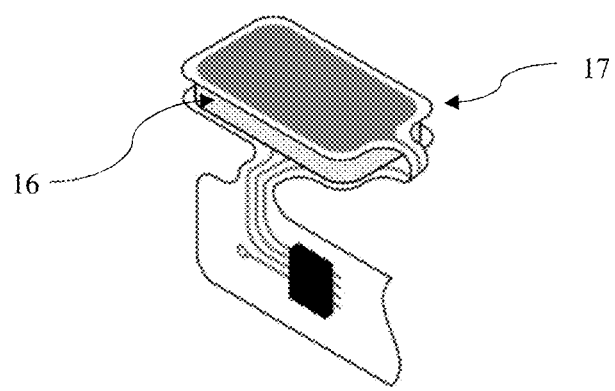
FIG. 6C illustrates a perspective view of a detail of the dielectric substrate with a sensor protected by a shielding pad.

The shielding pad is electrically separated from the ground pad. The shielding pad is further electrically separated from the sensing pad. Electrically separated refers to the situation wherein two conductors are electrically separated if the resistance measured between them is higher than 10 Ohm. Two conductors are electrically separated if they are not short-circuited. As illustrated in FIGS. 6A-C, the shielding pad is an active shielding electric conductor that shields the sensing pad from external electrical noise or disturbances. The shielding pad is used by the integrated circuit 10 to actively shield the sensing pad from external electrical noise as well as from the ground pad allowing that the electric field in the vicinity of the sensing pad is not altered by external factors such as noise or proximity to external bodies other than the proximity to the ground pad. The reduction of the effects due to the external disturbances by using the shielding pad allows enhancing the sensitivity of the sensing pad sensitivity. The active shielding pad is parallel or coplanar to the sensing pad and on the verso side of the sensing pad or area and electrically separated from the ground pad. The active shielding pad is electrically connected to the integrated circuits using said shielding pad to increase the sensitivity of the sensor and to reduce the effect of external disturbances.

Figure 7C:
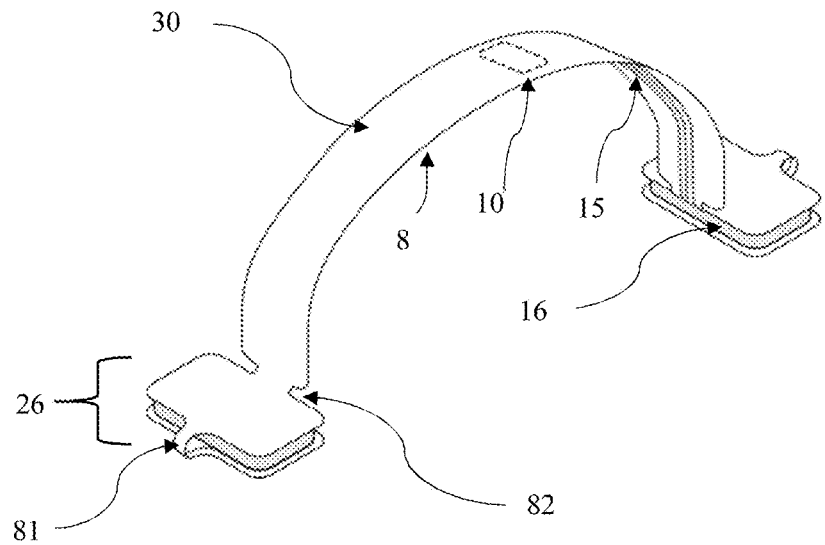
FIG. 7C shows a perspective view of a dielectric substrate according to a further embodiment intended for a dental appliance for the maxillary dental arch and/or the palate.
Figure 10A:
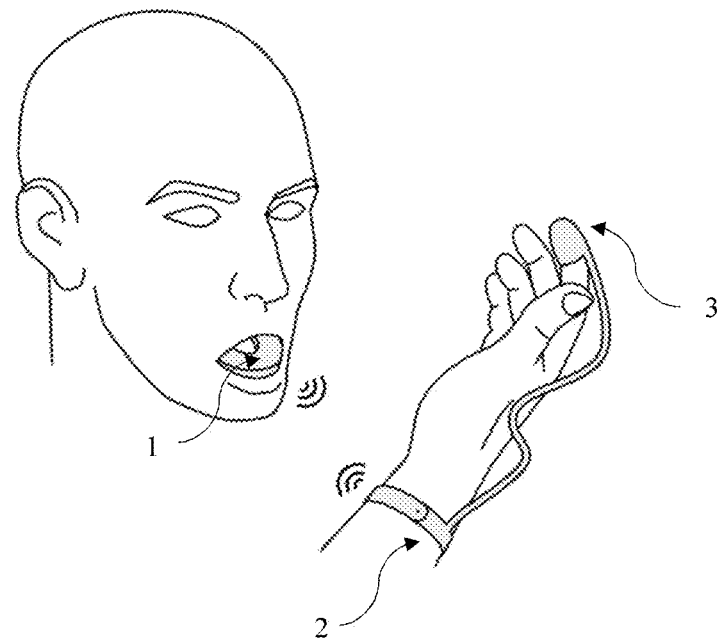
FIG. 10A and FIG. 10B illustrate device assemblies for reducing teeth clenching and/or grinding.
Figure 10B:
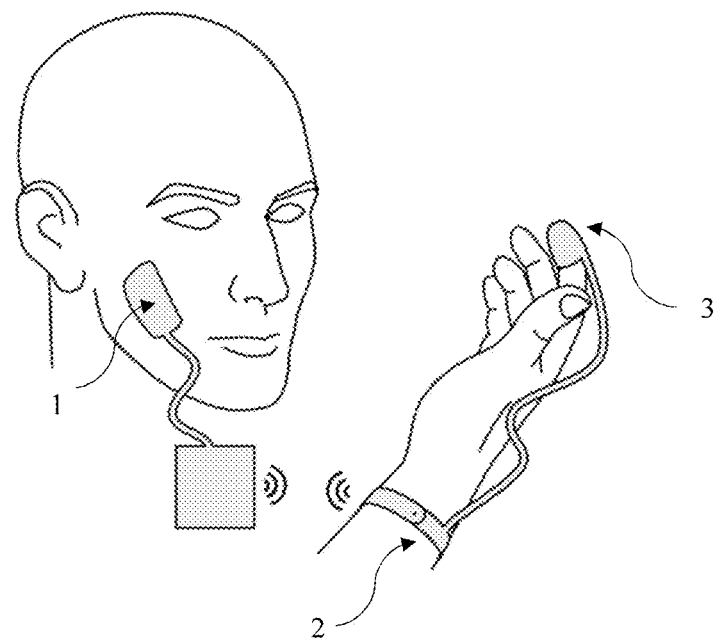

The sensing pad 14 is an electric conductor used by the integrated circuit 10 to sense a variation of charge or electric field or current or voltage. One sensing area may comprise or house one or more sensing pads 14, preferably two sensing pads per sensing area. The same dielectric substrate may house one or more sensing area which houses one or more sensing pads. If the same dielectric substrate houses more than one sensing areas as illustrated in FIG. 7A and FIG. 7C, said sensing areas are not continuous areas but separated sensing areas.

The ground pad 12 is an electric conductor used by the integrated circuit 10 to as a reference value for its operating. The material of the dielectric substrate is selected from semi-rigid material, flexible material or elastic material. Semi-rigid material is selected from glass-reinforced epoxy laminate material such as FR4 or from fluoropolymers, or polytetrafluoroethylene such as Teflon. Flexible material is selected from polyimide film, poly (4,4'-oxydiphenylene-pyromellitimide) film, such as Kapton or Kapton Polyimide. Elastic material is selected from polyurethanes, ethyl vinyl acetate, PDMS or silicones. The material of the dielectric substrate may be a printed circuit board with flexible regions and semi-rigid regions or a flexible printed circuit board.

The material of the sensing pad, ground pad and/or shielding pad is semi-rigid and flexible or elastic. The semi-rigid and flexible material is selected from metal with a thickness in the range of 1-80 µm, 1-10 µm, 2-20 µm, 5-50 µm, 4-60 µm, preferably 5 µm. The elastic material of the pad are selected from conductive polymers or metal with thickness in the range of 1-1800 nm, 10-1500 nm, 50-1000 nm, 100-200 nm, 500-1200 nm, preferably 1000 nm deposited on elastic substrates, conductive inks (conductive Silver ink) or liquid metals (e.g. Gallium). The material used for the pad is deposited on the dielectric substrate by a method involving lamination, evaporation, sputtering, screen printing or electro-deposition. The dielectric substrate areas housing the sensing pad and/or the ground pads are shaped by photolithography, laser cutting, etching, and by using a patterned mask. Polishing and finishing can be used to improve bio-compatibility.

The integrated circuit 10 may be soldered to the dielectric substrate or glued using conductive glue.

The elastic material 16 separating the sensing pad 14 and the ground pad 12 is selected from elastomer (e.g. silicone), polymer (e.g. Polyethylene), open cell foam (e.g. Polyethylene foam), closed cell foam (e.g. silicone foam) made by elastomeric material, polymeric material, flexible material, a conductive polymer (e.g. Silver ink, carbon black), a dielectric material (e.g. polyurethane, Ethyl vinyl acetate) or piezo-electric (e.g. Polyvinylidene fluoride, Sodium bismuth titanate, Gallium phosphate) material. The material is preferably selected to behave elastically, or to exhibit a flexible and elastic behavior in the human biting load range.

The sensor 26 comprises one or more sensing pads 14 and one or more ground pads 17 being conductive and separated by an elastic material. The sensing pad and the ground pad move closer to human bite as illustrated in FIG. 8B. When, the dental appliance comprising one or more sensor 26 is placed in the mouth, the human bite compresses the elastic material 16 of the sensor and the distance between the ground pad and the sensing pad changes.

By measuring the electrical capacitance and/or the electrical resistance between both sensing and ground pads, the dental load due to the human bite on the substrate can be qualitatively or quantitatively measured and monitored by a device assembly as described herein. With the capacitive sensing approach, a capacity increase is measured when biting load increases. With the resistive sensing approach, a resistance decrease is measured when the bite load increases, as expected by the Ohm's Law.

In one embodiment, the elastic material 16 separating the sensing pad and the ground pad in the sensor are dielectric and the integrated circuit 10 performs capacitive measurements between the sensing pad and the ground pad. Upon human bite, the sensing pad and the ground pad get closer, compressing the dielectric material. Thus, the capacitance gathered from the integrated circuit is increased. The dental load applied on the dental appliance may be estimated by a device assembly as described herein using Hooke's law. The presence of the shielding pad increases the sensitivity of the measurement and reduces the effect of external disturbances on the sensing pads.

According to a further embodiment, under pressure or bite pressure, the elastic material 16 of the sensor is compressed and the sensing pad 14 moves closer to the ground pad 12, modifying the mutual capacitance and/or electrical resistance between the sensing pad and the ground pad, and generating a dental forces signal conducted through the integrated circuit 10 to the transmitter and/or receiver means and/or to the data storage means.

The dielectric substrate 8 is a single body or a layer assembly that hosts and keeps in place the sensing parts of the sensor 26 being one or more sensing pads 14 and one or more ground pads 12, the signal processing part being one or more integrated circuit 10 and their electrical connections being electric lines 15. Electronics and sensory parts are manufactured on the same dielectric substrate using the same technological processes without extra soldering processes, which represent an advantageous manufacturing and assembly process and allowing increasing the quality of the electro-mechanical properties of the dental appliance such as mechanical tolerances, electrical noise level and reproducibility of the measurements.

Further the dental appliance presents an overall elasticity because of the materials of dielectric substrate. As the material in between the ground pad and the sensing pad is elastic, at least in the range of physiological and supraphysiological human bite loads, the deformation behaviour of the substrate under compressive load is repeatable yielding repeatable measurements and thus overcoming existing problems associated with the elevated hysteresis of existing intraoral sensors. Due to the dielectric substrate configuration and the elasticity of the materials in the inter-occlusal region, the measurements of the bruxism can be precise, accurate, quantitative, reliable and repeatable both for static and dynamic bite closure. The dental appliance is made of a material which may be Ethyl Vinyl Acetate (EVA).

As used herein, "human bite" or "bite" or "bite closure" or "bite occlusion" refer to the movement that let the upper and lower teeth meet when the jaw is closed. More specifically, it is the static or dynamic relationship between the maxillary (upper) and mandibular (lower) teeth when they approach each other, as occurs during, e.g., chewing or at rest. "Static bite" refers to the situation when forces are applied to the jaw and the jaw is closed and stationary, while "dynamic bite" (also termed as articulation) refers to jaw movements when the jaw is moving. These movements are intended in presence of inter-occlusal materials as well as in absence of inter-occlusal materials.

According to one embodiment, two or more sensors 26 are linked with each other through a portion of the dielectric substrate, said portion of the dielectric substrate comprising one or more electric areas 9 and/or integrated circuit 10 as illustrated in FIG. 7B.

In addition, the shape of the dielectric substrate can be designed to reduce the mechanical stress in the material of the dielectric substrate upon bending and upon dental load. Holes and metal appendices can be patterned on the substrate for the same purpose.

According to one embodiment, the dielectric substrate 8 is foldable and embedded in the dental appliance having an outer side 28, a sensor side 27 and an inner side 29, and, when said dental appliance is placed in the mouth, the outer side covers the buccal tooth surface, the sensor side covers the occlusal or incisal tooth surface and the inner side covers the lingual tooth surface and/or the palate. The one or more electric areas 9 are on said outer side 28 or on said inner side 29 of the dental appliance and the sensors are on said sensor side 27 of the dental appliance. The expression "on" does not limit the position of the one or more electric areas 9 to the inner or outer surface of said respective outer, inner or sensor side of the dental appliance. Said one or more electric areas can be embeddable into the material of the dental appliance. Such embodiments are illustrated in FIG. 9, dielectric substrate embedded in the appliance, as well as in FIG. 7B, folded dielectric substrate not being embedded or included in a dental appliance.

According to a further embodiment, the dental appliance fits the mandibular arch or fits the maxillary dental arch and/or the palate, the sensors 26 being on the sensor side 27 and/or directed on the occlusal and/or incisal tooth surface. The dental appliance fitted the dental arch and/or the palate of the superior maxillary may comprise a dielectric substrate 8, wherein one or more electric areas are on a portion 30 of the dielectric substrate fitted the palate as illustrated in FIG. 7C connecting at least two sensors 26. Said dental appliance for the superior maxillary may have an inner side covering totally the lingual tooth surface and the palate or partially the lingual tooth surface and the palate, fitting only a part of the dental arch. Thus the dielectric substrate included in the dental appliance is conformed to the dental arch shape or to a portion of the dental arch shape to better fit in the user's mouth.

According to another embodiment, the dental appliance further comprises one or more transmitter and/or receiver means 221, such as Bluetooth LE, one or more data storage means 222, such as flash memory or EEPROM memory, and a battery power source 23, such as Lithium polymer battery. Such a dental appliance is illustrated in FIG. 9. The battery is preferably a rechargeable battery. The dental appliance further comprises circuitry to recharge the battery. The battery is wirelessly recharged in order to maintain the dental appliance insulated and waterproof.

According to one embodiment, the integrated circuit 10 connected to the sensing pad measures the mutual capacitance and/or the electrical resistance between said sensing pad and the ground pad, generating a signal being conducted to the transmitter and/or receiver means and/or to the data storage means. The mechanical load evaluated by the sensing pad is used to determine the condition of bruxism during sleep or wakefulness. A threshold or a time interval duration or both can be used to characterize the condition of bruxism.

Multiple sensing pads can be designed in the same substrate to cover different biting regions on the dental arch. The load gathered on the different sensing pads can be used to discriminate clenching of the jaw or maxillary from grinding or gnashing of the jaw or maxillary. The dynamics of the bite closure, such as force intensity, unbalances, direction of grinding, duration of events, sequence of events, types of bruxism pattern, is assessed by evaluating the load on the different sensing pads over time. The shape of the sensing pad and the mutual disposition of different sensing pads on the dielectric substrate are used to better evaluate the dynamics of the bite closure.

According to a further embodiment, under pressure or bite pressure, the elastic material 16 of the sensor is compressed and the sensing pad 14 moves closer to the ground pad 12, modifying the mutual capacitance and/or electrical resistance between the sensing pad and the ground pad, and generating a dental forces signal conducted through the integrated circuit 10 to the transmitter and/or receiver means 221 and/or to the data storage means 222. Such embodiments are illustrated in FIGS. 8A-8B According to a further embodiment, the dental appliance is used for monitoring dental contact, dental forces, and/or for detecting teeth clenching and/or grinding.

The present invention also relates to a device and a method to accurately evaluate patient sleep and the patient sleeping state in order to anticipate the bio-feedback response before bruxism events occur. This can be obtained by recording one or more patient parameters, continually correlating these data, evaluating the sleep state of the patient and triggering a bio-feedback action that anticipates in time a bruxism event. In addition, the bio-feedback can be activated as a consequence of bruxism detection. The biofeedback action can be terminated after a determinate amount of time or as soon as the sleep parameters return at normal/nominal levels.

The present invention also relates to a device assembly for reducing teeth clenching and/or grinding and/or preventing bruxism comprising a sensing unit 1 for detecting teeth clenching and/or grinding, a biofeedback unit 2, at least one auxiliary unit 3, and a signal processing means, characterized in that said sensing unit, said biofeedback unit, said at least one auxiliary unit and said signal processing means are included in one device or in two or more devices; in that the at least one auxiliary unit is a sensor for measuring one or more sensor signals selected from respiratory airflow, snoring, blood oxygen saturation, pH, blood pressure, heart rate, electrocardiographic activity, electroencephalographic activity, body temperature, body position, body movement, and eye movement; in that the signal processing means comprises a receiver means to detect one or more sensor signals, and/or one or more dental forces signals, a monitoring means to detect the variation of the intensity and/or the frequency of said signals vs. time, and a transmitter means to generate an action signal in response to said one or more variations of one or more sensor signals and/or said dental forces signals; and in that the biofeedback unit is a responsive means in communication with the signal processing means and responding to the action signal and is selected from means providing vibrating signal, tactile signal, acoustic signal, electrical stimulation signal and/or optical signal.

The sensing unit 1 of the device assembly for reducing teeth clenching and/or grinding and/or preventing bruxism may comprise a masticatory muscle activity monitoring unit or jaw activity monitoring unit and/or dental forces monitoring unit. The masticatory unit may be included in the same device as the device included the sensing unit 1, the biofeedback unit 2, the at least one auxiliary unit 3 and/or the signal processing means. The masticatory muscle monitor unit comprises one or more electrodes and/or one or more intra-oral sensors measuring electromyography (EMG) signal.

When the device assembly comprises a masticatory muscle activity monitor unit, the signal processing means comprises a receiver means to detect one or more EMG signals, one or more sensor signals, and/or one or more dental forces signals, a monitoring means to detect the variation of the intensity and/or the frequency of said signals vs. time, and a transmitter means to generate an action signal in response to said variation of said EMG signals, said sensor signals and/or said dental forces signals.

The biofeedback unit 2 is a responsive means in communication with the signal processing means and responding to the action signal and is selected from means providing vibrating signal, tactile signal, acoustic signal and/or optical signal.

In one embodiment, the sensing unit 1 comprises the dental appliance 4. The dental appliance may be used as dental forces monitoring unit. The sensing unit may be then integrated in the dental appliance comprising the sensors or the sensors for bruxism detection. The biofeedback unit 2 and the at least one auxiliary unit 3 and/or the signal processing means may be integrated in the dental appliance or in one or more further devices. Such embodiment is illustrated by FIG. 1A-D.

In a further embodiment, the dental appliance 4 further comprises the sensing unit 1, the biofeedback unit 2 and/or the at least one auxiliary unit being on a second and/or a third device selected from wearable devices: band, wristband and/or captor or sensor wearable by a body part.

The sensing unit 1, the bio-feedback unit 2 and the auxiliary unit 3 may be included in an electronic board inside the dental appliance 4. When the sensing unit 1 comprise a masticatory muscle activity monitoring unit or jaw activity monitoring unit, said masticatory muscle activity or jaw activity monitoring unit may be included in the dental appliance 4, whereas the biofeedback unit 2 and the auxiliary unit 3 are included in a watch or bracelet or wristband. In another embodiment, the masticatory muscle activity or jaw activity monitoring unit and the auxiliary unit 3 are included in the dental appliance 4, whereas the bio-feedback unit 2 is integrated into the bracelet or watch or wristband. In a further embodiment, the masticatory muscle activity or jaw activity monitor unit is included in the dental appliance 4, the bio-feedback unit 2 is integrated into the bracelet or watch or wristband and the auxiliary unit 3 is wirelessly connected to the bracelet or watch or wristband. Wearable devices may be selected from, but not limited to, bracelet, watch, wristwatch, band, chest belt, head belt, ring, chest strip, head strip, rings, smartphone, and portable. In a further embodiment, the sensing unit 1 may comprises a masticatory muscle activity or jaw activity monitoring unit being separated from the dental forces monitoring unit or integrated in a further wearable device as defined above, said dental forces monitoring unit being integrated in or being the dental appliance, and said masticatory muscle activity or jaw activity monitoring unit being wirelessly connected with the dental appliance, the biofeedback unit and/or the auxiliary unit.

According to one particular embodiment, the masticatory muscle activity monitor unit is included in the dental appliance.

Intraoral sensors integrated or included in the smart appliance are used to detect the jaw activity. Bruxism is detected by force sensors or transducers integrated into the dental appliance 4.

The sensing unit 1, the bio-feedback unit 2, the signal processing means, and the at least one auxiliary unit 3 can be physically connected with wires, electrical lines or conductive traces and/or wirelessly connection such as radio means. The sensing unit 1 electronically measures and evaluates the activity of the patient jaw. Said monitor unit 1 provides a signal when the patient clenches, taps or grinds the teeth through EMG measurements (electromyography) or through the intraoral sensors or force transducer included in the dental appliance 4 and measuring dental biting forces. The jaw activity can be measured qualitatively or quantitatively.

The bio-feedback unit 2 provides an alert signal or a stimulus in response to the received signal from the signal processing means receiving the signals from the sensing unit, the intraoral sensor, the masticatory muscle activity monitor, and/or the auxiliary unit, or from all, one or more units, sensor or monitor, prior and/or during a bruxism event, preferably prior to said event. The alert signal or stimulus is provided to a means to vibrate and/or to operate in a tactile manner, acoustically, optically and/or electrically. Said means may be a part of the biofeedback unit or is connected to the biofeedback unit wirelessly or through electric lines. Multiple bio-feedback signals (i.e. acoustic and vibration) can be combined to alert or signal the same event. Said signals are provided to the user of the device assembly or to a further monitor.

The signal processing means can also post-process the data provided by the sensors and can be used for generating a report on the analysis of the bruxism, sleep and/or awake conditions. Said means integrates the different signals for one or more sensors in function of time or versus (vs.) time and detects variations. Said data may be processed by the monitoring means of the signal processing means.

The auxiliary unit is a sensor measuring at least one of the following body parameters: respiratory airflow, snoring activity, blood oxygen saturation, blood pressure, acid concentration, acid presence, pH, oral internal temperature, body temperature, blood pressure, heart rate, electroencephalographic activity, electrocardiographic activity, eyes movements, and movements. A single sensor in one auxiliary unit may provide information on multiple parameters. A pulse oximeter, e.g., sensor can provide information on blood oxygen saturation, blood pressure and heart rate. The analysis of the measurements of one or more of these parameters and their integration versus time, the recording of any variation of these parameters and their integration compared with a threshold determined in conditions without bruxism provide information to determine the state of the patient at a specific moment or during a period. This analysis is performed in the signal processing means or unit in order to provide the system with data that inform the bio-feedback unit and activates it before the occurrence of bruxism events.

As used herein, the wording "operatively connected", "operatively connectable" or even "operatively connecting", reflects a functional relationship between two or more components of a device or a system, that is, such a wording means that the claimed components must be connected in a way to perform a designated function. The "designated function" can change depending on the different components involved in the connection; for instance, the designated function of a microcontroller unit operatively connected to a display system is the (re-)elaboration and dispatch of the data relative to dental occlusion and/or clenching coming from the sensor to said display system. In the same way, the designated function of transmission conductive lines operatively connecting a capacitive pad to a microcontroller unit (transmitter unit, signal processing unit) is the transmission of an electrical signal from one component (the sensor pad) to another (the microcontroller). The connection can be physical or wireless; for instance, the "designated function" of a wireless connection operatively connecting a mobile device to a wearable device is the transmission of an electromagnetic signal (e.g. to exchange data) from one device (the mobile device) to another (the smart appliance). A person skilled in the art would easily understand and figure out what are the designated functions of each and every component of the device or the system of the invention, as well as their correlations, on the basis of the present disclosure.

In another embodiment, the transmitter means of the signal processing means in the device assembly for reducing teeth clenching and/or grinding and preventing bruxism generates the action signal in response to the variation of EMG signals and/or sensor signals to actuate the biofeedback unit 2 before detecting a variation of the intensity and/or frequency of the dental forces signals vs. time and/or detecting teeth clenching and/or grinding.

In a further embodiment, the biofeedback unit 2 in the device assembly for reducing teeth clenching and/or grinding and/or preventing bruxism is actuated in response of the action signal providing by the signal processing means detecting a variation of the intensity and/or the frequency of EMG signals.

In one embodiment, the transmitter means of the signal processing means in the device assembly for reducing teeth clenching and/or grinding and/or preventing bruxism generates the action signal in response to the variation of the intensity and/or frequency of dental forces signals vs. time.

To control the efficiency of the device assembly in the prevention of the bruxism, the dental forces signals from the sensing unit are monitored after actuating the biofeedback unit 2 in response to the variation of EMG signals and/or sensor signals. In the case of recording a variation of dental forces by the signal processing unit, the biofeedback unit is activated to suppress any residual variation of the dental forces signal or bruxism.

In a further embodiment, the sensor signals are selected from electroencephalographic activity, heart rate and blood oxygen saturation.

The present invention also provides a method for reducing teeth clenching and/or grinding and/or preventing bruxism comprising the steps of obtaining at least one sensor signal selected from respiratory airflow, snoring, blood oxygen saturation, pH, blood pressure, heart rate, electrocardiographic activity, electroencephalographic activity, body temperature, body position, body movement, and eye movement measured by an auxiliary unit;

processing at least one sensor signal and determining at least a variation of the intensity and/or the frequency of said signals vs. time;

providing a stimulus selected from vibrating signal, tactile signal, acoustic signal, electrical stimulation signal and/or optical signal in response to the variation of the intensity and/or the frequency at least one sensor signal vs. time.

The method for reducing teeth clenching and/or grinding and/or preventing bruxism may further comprise a step of obtaining a signal of the bruxism activity through measures with one or more electrodes and/or one or more intra-oral sensors, and/or a step of obtaining EMG signal of masticatory muscles activity through measures with one or more electrodes and/or one or more intra-oral sensors. Said steps may be prior or after the step of obtaining at least one sensor signal. Thus the method involving a step of obtaining a signal of bruxism activity and/or EMG signals, comprises a step of processing EMG signals and at least one sensor signal and determining at least a variation of the intensity and/or the frequency of said signals vs. time, and/or providing a stimulus selected from vibrating signal, tactile signal, acoustic signal and/or optical signal in response to the variation of the intensity and/or the frequency of said EMG signals and said at least one sensor signal vs. time.

The variation is determined according to a threshold of the particular signal measured in conditions without bruxism. During the application of the method, body parameters (e.g. but not limited to heart rate, blood oxygen saturation) during sleep are monitored and analysed. In health sleep stages, the heart rate variation in time is minimal, about 2% per minute, as well as the oxygen saturation assume value greater than 95%. Before a bruxism event, the heart rate changes, i.e. significantly increases in one minute (short time interval), e.g. from 55 beats per minute (bpm) to 65 bpm in one minute. Before a bruxism event, the oxygen saturation in blood significantly drops in one minute (short time interval), e.g. from 95% to 91% in one minute. Said variations occur in an 8-minute time window before a bruxism event. By tracking this time window before a bruxism event, the method described herein may be used for reducing teeth clenching and/or grinding and/or preventing bruxism by the occurrence of a bruxism event. The activation of a biofeedback unit may be triggered prior to the occurrence of bruxism.

According to one embodiment, the method of the invention to prevent bruxism comprises further steps of obtaining dental forces signals by measuring teeth pressure, processing dental forces signals and determining a variation of the intensity and/or the frequency of said dental forces signals vs. time. The dental forces signals are obtained by the dental appliance 4. The dental forces may be monitored during the monitoring or the steps of obtaining the EMG signals or one or more signals from one or more auxiliary units and/or after the step of providing a stimulus.

The action signal or stimulus from biofeedback unit is provided before the beginning of the bruxism or the occurrence of the bruxism episodes. The biofeedback unit may be also activated or actuated by receiving solely the information provided by the jaw activity monitoring unit without being activated by the signals provided by the sensing unit and/or by the auxiliary units. This prevents unexpected and unpredicted bruxism events to cause excessive damage to the teeth of the user. In order to reduce bruxism events, occurring without being able to be predicted, the device assembly may be used also for triggering the biofeedback unit upon bruxism detection of said residual bruxism event. This will shorten the duration of the detected event and prevent successive events from occurring. Moreover, the activation of the biofeedback unit before the occurrence of bruxism episodes and/or in response to unpredictable bruxism episodes allows to reduce the mechanical overload induced by bruxism on teeth and dental prostheses and/or, secondary effects encountered shortly before bruxism such as increased blood pressure, oxygen desaturation in blood and tachycardia, which may also improve the overall quality of the user sleep.

Figure 11A:
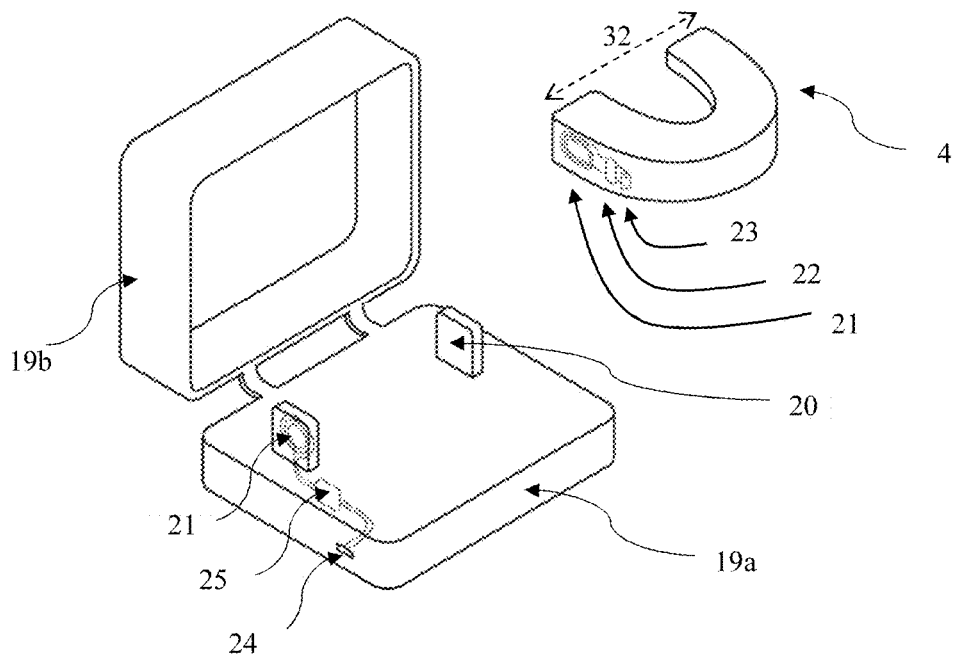
FIG. 11A illustrates a dental appliance storage case and a dental appliance.
Figure 11B:
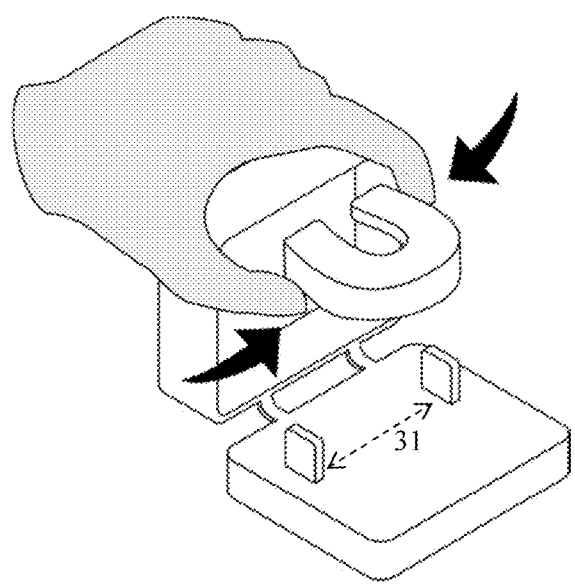
FIG. 11B and FIG. 11C illustrate the positioning of the dental appliance being flexible in the dental appliance storage case.
Figure 11C:
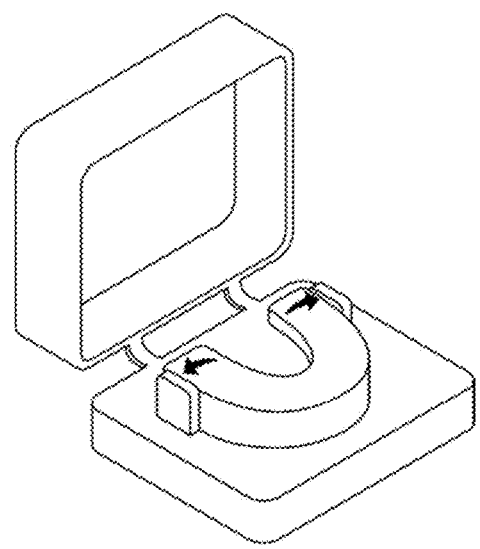
Figure 12B:
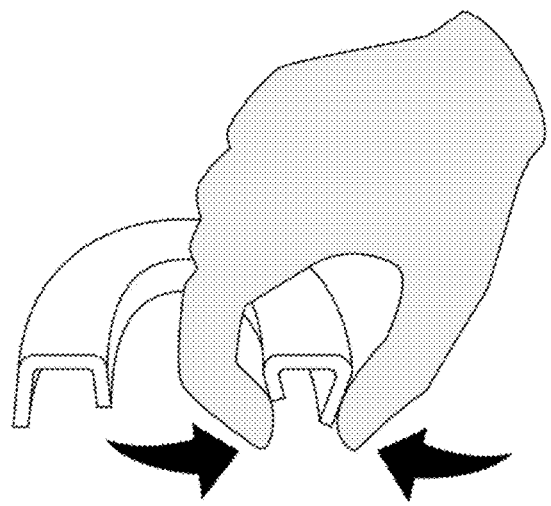
FIG. 12B and FIG. 12C respectively illustrate the flexibility of the dental appliance and the positioning of the said dental appliance in the dental appliance storage case.

The present invention also provides a dental appliance storage case or housing piece that wirelessly charges the dental appliance's battery and maintains the dental appliance in charging mode by applying elastic deformation to the whole appliance or to one of its parts as illustrated in FIGS. 11B-11C and 12B.

The dental appliance storage case comprises a base 19a; a cover hinged 19b to the base; two appendices 20 orientated normal to the base 19a;
characterized in that
the base comprises a power supply 24, a module to exchange data 25 and/or a means for producing alternating current;
at least one appendix comprises a coil 21 electrically connected to the power supply, the two appendices being separated by a distance 31 inferior to the distance 32 separating one outer edge to the other outer edge of the ends of a dental appliance, said dental appliance 4 comprising a coil 211 connected to a battery 23 and being flexible. The base 19a may further comprise a power input port. The fact that the dental appliance is flexible allows the appendices to clamp said dental appliance.

In the dental appliance storage case, according to one embodiment, the dental appliance is maintained in-between said two appendices during the charging of the battery and/or transport, the area comprising the coil at the end of the dental appliance matching with the area comprising the coil of the appendix.

During charging of the battery, the dental appliance comprising a storage means 22 is operatively connected to the module 25 of the storage case and/or with a mobile device to exchange data.

The appendices normal to the base of the storage case constrain, align or guide the dental appliance by elastically deforming it and forcing it to be placed in-between. Such position is a charging position and thus allows the splint to be held in place and stably maintained in charge mode. Being the splint kept in a well-defined position inside the storage case, the wireless charge is more efficient, the splint material does not overheat and any little inadvertent, undesired or unwanted bump or shake of the storage case does neither stop, nor interrupt the charging process of the splint, and does not affect the efficiency of the charging process itself.

Figure 12C:
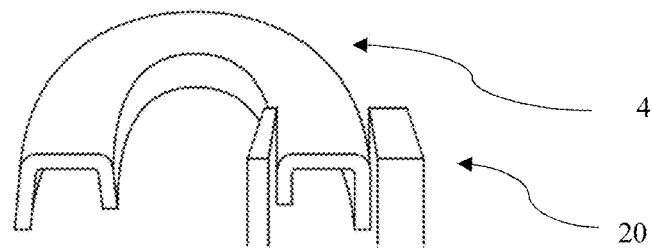

According to a further embodiment, the base may comprise four appendices normal to the base, two appendices being placed on both sides (inner and outer sides) of the dental appliance ends as illustrated in FIG. 12C. The inner sides and outer sides of the ends of the dental appliance are squeezed each between said two appendices. One or two appendices may comprise the coil 21 for charging the battery of exchanging data, said one or two appendices comprising the coil 21 being towards the external side of the case The storage case is being made of plastic. The charging circuit is composed by a DC (direct current) power supply, by an oscillator and a coil. The charging circuit is embedded in the storage case. The module exchanging data with the charging circuit stabilizes the voltage, and a battery. This circuit is embedded in the dental appliance.

The invention claimed is:
1. A dental appliance, comprising:
a dielectric substrate, comprising:
one or more electric areas comprising one or more integrated circuits and one or more electric lines;
one or more ground areas comprising one or more ground pads; and
one or more sensing areas comprising one or more sensing pads;
wherein:
the one or more electric areas, the one or more ground areas, and the one or more sensing areas are housed on the same dielectric substrate being in one piece and comprising a dielectric material;
one or more sections of the dielectric substrate are bent;
one of the one or more sensing areas faces one of the one or more ground areas; and
said one sensing area facing said one ground area is separated by a layer comprising an elastic material, and forms a sensor; and
wherein the one or more ground pads and the one or more sensing pads are electrically connected to one or more integrated circuits through the electric lines.

2. The dental appliance according to claim 1, wherein the one or more electric areas, the one or more ground areas, and the one or more sensing areas are housed on the same side of the dielectric substrate, said side being a front side.

3. The dental appliance according to claim 1, wherein two or more sensors are linked with each other by a portion of the dielectric substrate, said portion of the dielectric substrate comprising one or more electric areas and/or integrated circuits.

4. The dental appliance according to claim 1, further comprising one or more of a transmitter and/or a receiver, one or more data storage means, and a battery power source.

5. The dental appliance according to claim 4, wherein the one or more integrated circuits connected to the one or more sensing pads measures a mutual capacitance and/or an electrical resistance between said one or more sensing pads and the one or more ground areas, thereby generating a signal conducted to the transmitter and/or the receiver and/or to the data storage means.

6. The dental appliance according to claim 4, wherein, under pressure or bite pressure, the elastic material of the sensor is compressed and the sensing pad moves closer to the ground pad, thereby modifying a mutual capacitance and/or an electrical resistance between the sensing pad and the ground pad, and generating a dental forces signal conducted through the integrated circuit to the transmitter and/or the receiver and/or to the data storage means.

7. The dental appliance according to claim 1 adapted for monitoring dental contact, dental forces, and/or for detecting teeth clenching and/or grinding.

8. A device assembly for reducing teeth clenching and/or grinding and/or preventing bruxism, the device assembly comprising:
a sensing unit for detecting teeth clenching and/or grinding, the sensing unit comprising the dental appliance of claim 1;
a biofeedback unit;
at least one auxiliary unit; and
a signal processing means;
wherein:
said sensing unit, said biofeedback unit, said at least one auxiliary unit and said signal processing means are included in one device or in two or more devices;
the at least one auxiliary unit is a sensor for measuring one or more sensor signals selected from respiratory airflow, snoring, blood oxygen saturation, pH, blood pressure, heart rate, electrocardiographic activity, electroencephalographic activity, body temperature, body position, body movement, and eye movement;
the signal processing means comprises a receiver to detect one or more sensor signals, and/or one or more dental forces signals, a monitoring means to detect the variation of the intensity and/or the frequency of said sensor signals versus time, and a transmitter to generate an action signal in response to said one or more variations of one or more sensor signals and/or said dental forces signals; and
the biofeedback unit is a responsive means in communication with the signal processing means and responding to the action signal and is selected from means providing vibrating signal, tactile signal, acoustic signal, electrical stimulation signal and/or optical signal; and
the transmitter of the signal processing means generates the action signal in response to the variation of sensor signals to actuate the biofeedback unit before detecting a variation of the intensity and/or frequency of the dental forces signals versus time and/or detecting teeth clenching and/or grinding.

9. The device assembly according to claim 8, wherein the biofeedback unit is actuated in response to the action signal provided by the signal processing means detecting a variation of the intensity and/or the frequency of said sensor signals.

10. The device assembly according to claim 8, wherein the transmitter means of the signal processing means generates the action signal in response to the variation of the intensity and/or frequency of the dental forces signals versus time.

11. The device assembly according to claim 8, wherein the sensor signals are selected from electroencephalographic activity, heart rate and blood oxygen saturation.

12. A dental appliance storage case, comprising:
a base;
a cover hinged to the base; and
two appendices orientated normal to the base;
wherein:
the base comprises a power supply, a module to exchange data and/or a means for producing alternating current; and
at least one appendix comprises a coil electrically connected to the power supply, the two appendices being separated by a distance inferior to the distance separating one outer edge to the other outer edge of the ends of the dental appliance according to claim 1, said dental appliance comprising a coil connected to a battery and being flexible.

13. The dental appliance storage case according to claim 12, wherein said the dental appliance is maintained in-between said two appendices during the charging of the battery and/or transport, the area comprising the coil at the end of the dental appliance matching with the area comprising the coil of the appendix.

14. The dental appliance storage case according to claim 12, wherein, during charging of the battery, the dental appliance comprising a storage means is operatively connected to the module of the storage case and/or with a mobile device to exchange data.

15. A method for reducing teeth clenching and/or grinding and/or preventing bruxism, the method comprising the steps of:
obtaining at least one sensor signal selected from respiratory airflow, snoring, blood oxygen saturation, pH, blood pressure, heart rate, electrocardiographic activity, electroencephalographic activity, body temperature, body position, body movement, and eye movement measured by an auxiliary unit;
processing at least one sensor signal from the auxiliary unit and determining at least a variation of the intensity and/or the frequency of said signals versus time;
providing, prior to a bruxism event, a stimulus selected from vibrating signal, tactile signal, acoustic signal, electrical stimulation signal and/or optical signal in response to the variation of the intensity and/or the frequency of said at least one sensor signal versus time by actuating the biofeedback unit;
obtaining dental forces signals by measuring teeth pressure with the dental appliance according to claim 1;
processing dental forces signals; and
determining a variation of the intensity and/or the frequency of said dental forces signals versus time.

16. The method according to claim 15, wherein the dental forces signals are monitored during the monitoring of one or more signals from a masticatory muscle activity monitor unit and/or from one or more auxiliary units and/or after the step of providing a stimulus.

17. A dental appliance, comprising:
a dielectric substrate, comprising:
one or more electric areas comprising one or more integrated circuits and one or more electric lines;
one or more ground areas comprising one or more ground pads; and
one or more sensing areas comprising one or more sensing pads;

wherein:
 the one or more electric areas, the one or more ground areas, and the one or more sensing areas are housed on the same dielectric substrate being in one piece and comprising a dielectric material;
 one or more sections of the dielectric substrate are bent;
 one of the one or more sensing areas faces one of the one or more ground areas; and
 said one sensing area facing said one ground area is separated by a layer comprising an elastic material, and forms a sensor; and
wherein the dielectric substrate is foldable and embedded in the dental appliance having an outer side, a sensor side and an inner side, and, when said dental appliance is placed in the mouth, the outer side is configured to cover a buccal tooth surface, the sensor side is configured to cover an occlusal or incisal tooth surface and the inner side is configured to cover a lingual tooth surface and/or a palate; and in that the one or more electric areas are on said outer side or on said inner side of the dental appliance and the sensors are on said sensor side of the dental appliance.

18. A dental appliance, comprising:
 a dielectric substrate, comprising:
  one or more electric areas comprising one or more integrated circuits and one or more electric lines;
  one or more ground areas comprising one or more ground pads; and
  one or more sensing areas comprising one or more sensing pads;
 wherein:
  the one or more electric areas, the one or more ground areas, and the one or more sensing areas are housed on the same dielectric substrate being in one piece and comprising a dielectric material;
  one or more sections of the dielectric substrate are bent;
  one of the one or more sensing areas faces one of the one or more ground areas; and
  said one sensing area facing said one ground area is separated by a layer comprising an elastic material, and forms a sensor; and
 wherein the dental appliance fits a mandibular dental arch or is configured to fit a maxillary dental arch and/or a palate, the sensors configured for location on an occlusal and/or an incisal tooth surface.

* * * * *

UNITED STATES PATENT AND TRADEMARK OFFICE
CERTIFICATE OF CORRECTION

| | | |
|---|---|---|
| PATENT NO. | : 11,596,540 B2 | |
| APPLICATION NO. | : 16/955447 | |
| DATED | : March 7, 2023 | |
| INVENTOR(S) | : Marco Letizia et al. | |

It is certified that error appears in the above-identified patent and that said Letters Patent is hereby corrected as shown below:

On the Title Page

1. Item (22): "Dec. 22, 2017" Should be Dec. 18, 2018

2. Item (86): "PCT/IB2017/058358" Should be PCT/IB2018/060229

Signed and Sealed this
Ninth Day of May, 2023

Katherine Kelly Vidal
*Director of the United States Patent and Trademark Office*